US00PP31774P2

(12) United States Plant Patent
Vromans

(10) Patent No.: US PP31,774 P2
(45) Date of Patent: May 19, 2020

(54) STRAWBERRY PLANT NAMED 'LIMVALNERA'

(50) Latin Name: ***Fragaria* x *ananassa***
Varietal Denomination: LIMVALNERA

(71) Applicant: Jaap Vromans, Venlo (NL)

(72) Inventor: Jaap Vromans, Venlo (NL)

(73) Assignee: Asparagus Beheer B.V., Horst (NL)

( * ) Notice: Subject to any disclaimer, the term of this patent is extended or adjusted under 35 U.S.C. 154(b) by 0 days.

(21) Appl. No.: 16/350,433

(22) Filed: Nov. 15, 2018

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./208, 209
See application file for complete search history.

(56) References Cited

FOREIGN PATENT DOCUMENTS

QZ PBR 20160854 8/2018

OTHER PUBLICATIONS

UPOV-PLUTO: Plant Variety Database, Jul. 31, 2019, citation for 'LIMVALNERA'.*

* cited by examiner

*Primary Examiner* — Susan McCormick Ewoldt
(74) *Attorney, Agent, or Firm* — C. A. Whealy

(57) ABSTRACT

A new and distinct cultivar of Strawberry plant named 'LIMVALNERA', characterized by its upright and semi-open plant habit; moderately vigorous to vigorous growth habit; uniform fruit ripening; large long conical fruits that are glossy and bright red in color with seeds positioned at the fruit surface; pleasant fruit aroma and taste; good fruit postharvest longevity; and good transportation tolerance.

2 Drawing Sheets

Botanical designation: *Fragaria* x *ananassa.*
Cultivar denomination: 'LIMVALNERA'.

BACKGROUND OF THE INVENTION

The present Invention relates to a new and distinct cultivar of Strawberry plant, botanically known as *Fragaria* x *ananassa,* and hereinafter referred to by the name 'LIMVALNERA' and typically produced for fresh market consumption.

The new Strawberry plant is a product of a planned breeding program conducted by the Inventor in Horst, The Netherlands and Lepe, Spain. The objective of the breeding program was to develop new Strawberry plants with good fruit quality, ease of harvesting, good postharvest longevity and transportation tolerance.

The new Strawberry plant originated from a cross-pollination in March, 2011 in Horst, The Netherlands of *Fragaria* x *ananassa*. 'Primoris', not patented, as the female, or seed, parent with *Fragaria* x *ananassa* 'Ventana', disclosed in U.S. Plant Pat. No. 13,469, as the male, or pollen, parent. The new Strawberry plant was discovered and selected by the Inventor as a single plant from within the progeny of the stated cross-pollination in a controlled environment in Lepe, Spain in April, 2012.

Asexual reproduction of the new Strawberry plant by vegetative cuttings (runners) in a controlled environment at Lepe, Spain since May, 2012 has shown that the unique features of this new Strawberry plant are stable and reproduced true to type in successive generations of asexual reproduction.

SUMMARY OF THE INVENTION

Plants of the new Strawberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'LIMVALNERA'. These characteristics in combination distinguish 'LIMVALNERA' as a new and distinct Strawberry plant:

1. Upright and semi-open plant habit.
2. Moderately vigorous to vigorous growth habit.
3. Uniform fruit ripening.
4. Large long conical fruits that are glossy and bright red in color with seeds positioned at the fruit surface.
5. Pleasant fruit aroma and taste.
6. Good fruit postharvest longevity.
7. Good transportation tolerance.

Plants of the new Strawberry differ primarily from plants of the female parent, 'Primoris', in the following characteristics:

1. Plants of the new Strawberry produce a higher percentage of quality fruits than plants of 'Primoris'.
2. Fruits of plants of the new Strawberry are larger and longer (less rounded) than fruits of plants of 'Primoris'.
3. Fruits of plants of the new Strawberry are darker red in color than fruits of plants of 'Primoris'.

Plants of the new Strawberry differ primarily from plants of the male parent, 'Ventana', in the following characteristics:

1. Plants of the new Strawberry have a semi-open plant habit whereas plants of 'Ventana' have an open plant habit.
2. Plants of the new Strawberry produce a higher percentage of quality fruits than plants of 'Ventana'.
3. Fruits of plants of the new Strawberry are longer than and not as flat as fruits of plants of 'Ventana'.

Plants of the new Strawberry can be compared to plants of *Fragaria* x *ananassa* 'Calinda', disclosed in U.S. Plant Pat. No. 26,904. In side-by-side comparisons, plants of the new Strawberry differ primarily from plants of 'Calinda' in the following characteristics:

1. Plants of the new Strawberry have a 50% higher fruit yield per plant than plants of 'Calinda'.
2. Fruits of plants of the new Strawberry are longer than fruits of plants of 'Calinda'.

BRIEF DESCRIPTION OF THE PHOTOGRAPHS

The accompanying colored photographs illustrate the overall appearance of the new Strawberry plant showing the colors as true as it is reasonably possible to obtain in colored reproductions of this type. Colors in the photographs may differ slightly from the color values cited in the detailed botanical description which accurately describe the colors of the new Strawberry plant.

The photograph at the top of the first sheet is a side perspective view of a typical fruiting plant of 'LIMVALNERA' grown in a container.

The photograph at the bottom of the first sheet is a close-up view of typical leaves of 'LIMVALNERA'.

The photograph at the top of the second sheet is a close-up view of typical flowers of 'LIMVALNERA'.

The photograph at the bottom of the second sheet is a close-up view of typical developing and developed fruits of 'LIMVALNERA'.

DETAILED BOTANICAL DESCRIPTION

The aforementioned photographs, following observations and measurements describe plants grown in 19-cm containers during the summer and early autumn in a polyethylene-covered greenhouse in Horst, The Netherlands and under cultural practices typical of commercial Strawberry production. During the production of the plants, day temperatures ranged from 15° C. to 35° C., night temperatures ranged from 4° C. to 20° C. and light levels ranged from 40 to 110 klux. Plants were one year old when the photographs and description were taken. In the following description, color references are made to The Royal Horticultural Society Colour Chart, 2015 Edition, except where general terms of ordinary dictionary significance are used.

Botanical classification: *Fragaria* x *ananassa* 'LIMVALNERA'.

Parentage:

*Female, or seed, parent.*—*Fragaria* x *ananassa* 'Primoris', not patented.

*Male, or pollen, parent.*—*Fragaria* x *ananassa* 'Ventana', disclosed in U.S. Plant Pat. No. 13,469.

Propagation:

*Type.*—By vegetative cuttings (runners).

*Time to initiate roots, summer.*—About three days at soil temperatures about 14° C. to 16° C. and ambient temperatures about 19° C. to 21° C.

*Time to produce a rooted young plant, summer.*—About two weeks at soil temperatures about 14° C. to 16° C. and ambient temperatures about 19° C. to 21° C.

*Root description.*—Medium in thickness, fleshy; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Perennial; upright and semi-open plant habit; overall shape, flattened globular; leaves basal; moderately vigorous to vigorous growth habit; moderate growth rate.

*Plant height.*—About 20.2 cm.

*Plant diameter* (*excluding stolons*).—About 34.5 cm.

Stolons:

*Length.*—About 32.3 cm.

*Diameter.*—About 3 mm.

*Texture.*—Sparsely to moderately pubescent.

*Color.*—Close to 144A to 144B tinged with close to N199D.

Leaf description:

*Arrangement and appearance.*—Basal rosette; compound with typically three leaflets per leaf; leaves are not variegated.

*Leaf length.*—About 12.9 cm.

*Leaf width.*—About 15.8 cm.

*Leaf shape.*—Tri-foliate, reniform in outline.

*Leaflet length.*—About 8.7 cm.

*Leaflet width.*—About 8.4 cm.

*Leaflet shape.*—Broadly ovate to nearly orbicular.

*Leaflet apex.*—Short abruptly acute.

*Leaflet base.*—Obtuse to short attenuate.

*Leaflet margin.*—Coarsely serrate to crenate.

*Leaflet texture and luster, upper surface.*—Sparsely pubescent; slightly rugose; slightly glossy.

*Leaflet texture and luster, lower surface.*—Moderately pubescent along venation; slightly rugose; matte.

*Leaflet venation.*—Pinnate.

*Leaflet color.*—Developing leaflets, upper surface: Close to 143A. Developing leaflets, lower surface: Close to between 143B and 144A. Fully expanded leaflets, upper surface: Slightly darker than between NN137A and 147A; venation, close to 144A. Fully expanded leaflets, lower surface: Close to between N138C and 191A; venation, close to 144D.

*Petioles.*—Length: About 10.8 cm. Diameter: About 3 mm. Texture and luster, upper and lower surfaces: Densely pubescent; moderately glossy. Strength: Strong, flexible. Color, upper and lower surfaces: Close to 144B.

*Stipules.*—Length: About 3.2 cm. Diameter: About 6 mm. Shape: Narrowly deltoid. Apex: Narrowly acute. Base: Broadly cuneate. Margins: Entire. Texture, upper surface: Smooth, glabrous. Texture, lower surface: Moderately pubescent. Color, upper and lower surfaces: Close to 146D; tinged towards the apex and margins with close to 180C.

Flower description:

*Flower form and flowering habit.*—Rotate flowers arranged in lateral trusses; flowers are positioned upright to outwardly and are held slightly below the foliar plane; about six flowers develop per truss.

*Truss height.*—About 9.2 cm.

*Truss diameter.*—About 6.9 cm.

*Fragrance.*—Faint, sweet and pleasant.

*Natural flowering season.*—Long flowering period; plants flower from the spring into the summer in The Netherlands; individual flowers last about one week on the plant.

*Flower diameter.*—About 2.9 cm.

*Flower depth (height).*—About 1.1 cm.

*Flower buds.*—Length: About 9 mm. Diameter: About 1.3 cm. Shape: Roughly ovoid. Texture and luster: Smooth, glabrous; sepals, sparsely pubescent; matte. Color: Close to 145D; sepals, close to 138B.

*Petals.*—Quantity and arrangement: Five in a single whorl. Length: About 1.4 cm. Width: About 1.5 cm. Shape: Nearly orbicular. Apex: Obtuse. Base: Cuneate. Margin: Entire; slightly undulate. Texture and luster, upper surface: Smooth, glabrous; moderately velvety; matte. Texture and luster, lower surface: Smooth, glabrous; moderately velvety; slightly glossy. Color: When opening, upper and lower surfaces: Close to NN155C. Fully opened, upper and lower surfaces: Close to NN155D; venation, close to NN155D.

*Sepals.*—Quantity, arrangement and calyx description: About ten sepals arranged in two whorls of five each; calyx, star-shaped; calyx adherence is weak; sepals are orientated away from the fruit. Calyx length: About 5 mm. Calyx diameter: About 2.8 cm. Length: About 1 cm to 1.1 cm. Width: About 5 mm to 7 mm. Shape: Broadly ovate to ovate. Apex: Acute. Base: Broadly cuneate. Margin: Entire; moderately pubescent. Texture and luster, upper surface: Smooth, glabrous; moderately glossy. Texture and luster, lower surface: Sparsely pubescent; matte. Color: When opening, upper surface: Close to 143A. When opening, lower surface: Close to 143B. Fully opened, upper surface: Close to 137A. Fully opened, lower surface: Close to 138A to 138B.

*Peduncles.*—Length: About 2.5 cm. Diameter: About 3 mm to 4 mm. Strength: Strong. Aspect: About 40° from leaf axil. Texture and luster: Densely pubescent; moderately glossy. Color, upper surface: Close to 144B tinged with close to 146C. Color, lower surface: Close to 144B.

*Pedicels.*—Length: About 3.2 cm. Diameter: About 2 mm. Strength: Moderately strong. Aspect: About 30° from the peduncle axis. Texture and luster: Sparsely to moderately pubescent; moderately glossy. Color: Close to 144A to 144B.

*Reproductive organs.*—Stamens: Quantity per flower: About 25. Filament length: About 2 mm. Filament color: Close to 150D. Anther size: About 0.8 mm by 0.5 mm. Anther shape: Broadly oblong Anther color: Close to 153C. Pollen amount: Scarce. Pollen color: Close to 153B. Pistils: Quantity per flower: About 160. Pistil length: About 1 mm. Style length: About 0.8 mm. Style color: Close to 153C. Stigma diameter: About 0.2 mm. Stigma shape: Club-shaped. Stigma color: Close to 153B. Ovary color: Close to 144B. Fruits and achenes: Fruiting truss length (including peduncle): About 17.5 cm. Fruiting truss diameter: About 12.5 cm. Fruiting truss color: Close to 143B. Quantity of fruits per truss: About 16. Natural fruiting season: Plants produce fruit from the mid-summer into the autumn in The Netherlands. Postharvest longevity: About nine days; good transportation tolerance. Length: About 3.3 cm. Diameter: About 2.9 cm. Cavity length: About 1.4 cm. Cavity width: About 5 mm. Shape: Long conical. Fruit weight per fruit, first quality: About 29.5 g. Fruit weight per plant, first quality: About 900 to 1,000 g. Firmness: Firm. Fragrance, taste: Pleasant; strongly sweet; good balance between sweetness and acidity. Brix: About 9.2° Bx. Luster: Glossy. Surface unevenness: Slightly. Color, outer surface: Close to 42A to 42B. Color, flesh: Close to 40B. Color, core: Close to 40D. Achene density and position: Medium density; about 150 achenes per fruit; achenes positioned level with the fruit surface. Achene length: About 1 mm. Achene diameter: About 0.75 mm. Achene texture and luster: Smooth, glabrous; glossy. Achene color: Close to 151A.

Pathogen and pest resistance: To date, plants of the new Strawberry have not been observed to be resistant to pathogens and pests common to Strawberry plants.

Temperature tolerance: Plants of the new Strawberry have been observed to tolerate temperatures ranging from −32° C. to 40° C. and are suitable for USDA Hardiness Zones 4 to 9.

It is claimed:

1. A new and distinct Strawberry plant named 'LIMVALNERA' as illustrated and described.

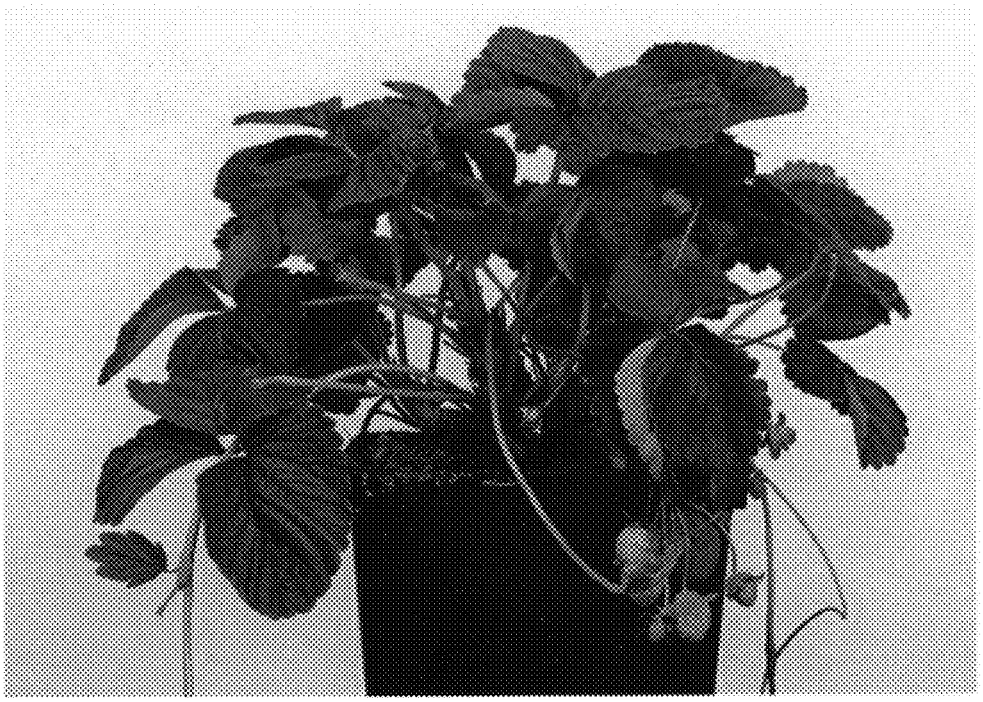
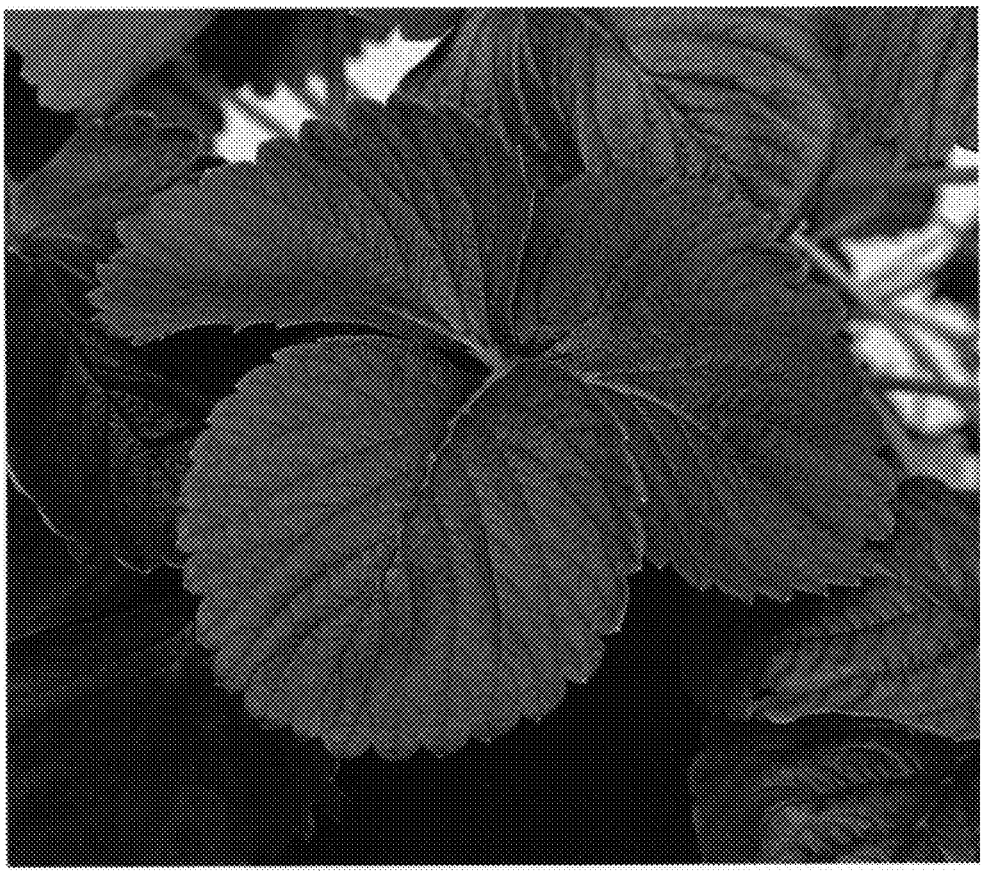

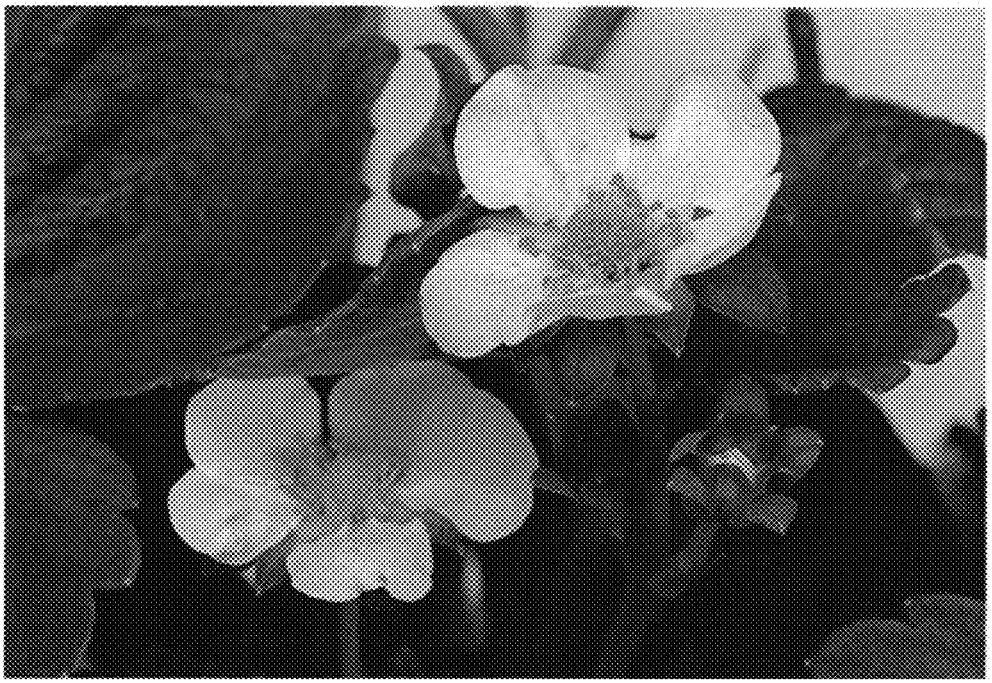
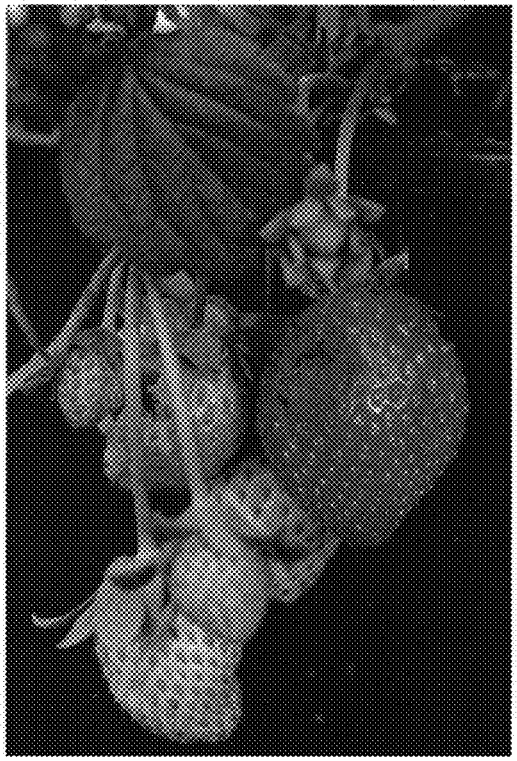

* * * * *